United States Patent [19]

Moses et al.

[11] Patent Number: 5,612,312

[45] Date of Patent: Mar. 18, 1997

[54] METHOD FOR TREATING INSULIN RESISTANCE WITH IGF-I

[76] Inventors: Alan C. Moses, 470 Quinobequin Rd., Waban, Mass. 02168; Linda A. Morrow, 11 Rice St., Newton, Mass. 02159; Jeffrey S. Flier, 14 Sylvan Ave., West Newton, Mass. 02165

[21] Appl. No.: 436,633

[22] Filed: May 8, 1995

Related U.S. Application Data

[62] Division of Ser. No. 279,831, Jul. 25, 1994, which is a continuation of Ser. No. 8,461, Jan. 25, 1993, abandoned.

[51] Int. Cl.$^6$ .................................................. A61K 38/30
[52] U.S. Cl. ............................................ 514/12; 514/866
[58] Field of Search .................................. 514/3, 12, 866; 530/303

[56] References Cited

U.S. PATENT DOCUMENTS 4,988,675  1/1991  Froesch ........................................ 514/4

FOREIGN PATENT DOCUMENTS

| 2252529 | 1/1993 | Australia . |
|---|---|---|
| 0331630 | 6/1989 | European Pat. Off. . |
| 0436469A1 | 7/1991 | European Pat. Off. . |
| 9103253 | 3/1991 | WIPO . |
| WO9325226 | 12/1993 | WIPO . |

OTHER PUBLICATIONS

Schoenle, E. J., et al., "Recombinant human insulin–like growth factor I (rhIGFI) . . . ", Diabetologia, pp. 675–679, 1991.

Usala, Anton–Lewis, et al., "Brief Rpt.: Treatment of Insulin–Resistant Diabetic . . . "; NEJM, vol. 327, No. 12, pp. 853–857, 1992.

Zenobi, Peter, et al., "Insulin–like Growth Factor—I . . . "; J. Clin. Invest., vol. 90, pp. 2234–2241, Dec. 1992.

Zenobi, Peter, et al., "Effects of IGF–I on Glucose Tolerance . . . " J. Clin. Invest., vol. 89, pp. 1908–1913, Jun. 1992.

Schalch, Don S., et al., "Short–term metabolic effects of rhIGF–I". Modern Concepts of IGF, pp. 705–713, 1991.

Elahi, D., et al., "Hemodynamic and Metabolic Responses to Human IGFI . . . "; Modern Concepts of IGF, pp. 219–224, 1991.

Quin, John et al., "Acute Response to IGF–I in a Patient . . . ", Correspondence Section; NEJM, vol. 323, No. 20, pp. 1425–1426, 1990.

*Primary Examiner*—Marianne P. Allen
*Assistant Examiner*—Karen E. Brown
*Attorney, Agent, or Firm*—Lorusso & Loud

[57] ABSTRACT

A method of chronic modification of cell barrier properties by exposing a cell to a modification-effective amount of IGF-I for at least about 7 days wherein the modification effective amount is between about 50 μg/kg and less than about 500 μg/kg is disclosed. Further disclosed is a method of chronic amelioration or reversal of insulin resistance as well as a method of diagnosing and screening for rhIGF-I sensitive cell barrier properties.

2 Claims, 10 Drawing Sheets

FIG. 9

| TEST | D-4 | D-3 | D-2 | D-1 | D0 | D+1 | D+2 | D+3 | D+7 | D+8 | D+9 | D19 | D26 | D27 | D28 | D29 | D30 |
|---|---|---|---|---|---|---|---|---|---|---|---|---|---|---|---|---|---|
| PE | • | • | | | | | | | | | | | | | | | |
| LAB | • | • | | • | | | | | | | | | | | | | |
| IVGTT | | • | | | | | | | • | | | • | • | | | | |
| SUSTACAL | | • | | | | | | | • | • | | | | | • | | |
| IV-ITT | | | | • | | | | | | • | | | | | | | • |
| IV-ITT #2 | | | | | • | | | | | | | | | | • | | |
| 24 HR UA | | | • | • | • | • | • | | | • | | • | | | | | |
| RMR | | • | | | | | | | | | | | | • | | | • |
| ANTHRO | | • | | | | | | | | | | | | | | | |
| SSPG | | | • | | | | | | | | | | | • | | | |
| GLU-INS | | | | | • | | | | | | | | | • | | | |
| AN/PHOTO | | • | | | | | | | | | | | | | | | • |
| IGF-I SCRx | | | | • | | • | • | • | • | • | • | • | • | • | • | • | • |
| INPATIENT | • | • | • | • | • | • | • | • | • | • | • | • | • | • | • | • | • |
| DISCHARGE | | | | | | | | • | | | • | | | | | | • |

METHOD FOR TREATING INSULIN RESISTANCE WITH IGF-I

This is a divisional of application Ser. No. 08/279,831 filed Jul. 25, 1994, which is a continuation of application Ser. No. 08/008,461 filed Jan. 25, 1993, now abandoned.

BACKGROUND

Many diseases have a secondary effect on cell barrier properties. For example, Diabetes mellitus can create a condition where a resistance to insulin exists or develops whereby the normal cell barrier mechanisms fail. In many such cases, adequate amounts of insulin are available but the insulin is not able to perform its usual function. The explanations for this vary widely and, similarly, the therapeutic approaches to treating such conditions also vary widely. In cases of insulin resistance, several approaches are presently known in the art but no single approach has proven universally acceptable. Some approaches include diet and exercise, oral hypoglycemic agents, alpha glucosidase inhibitors, fenfluramine, fatty acid oxidation inhibitors, atypical selective beta-adrenoceptor agonists, phenytoin sodium, captopril, an oxidized form of the trace element Vanadium (such as Vanadate) or a glucuretic agent (such as Phlorizin) and Insulin-like growth factors I and II. The summarization of the mode of administration and action of these various approaches which follows assists in the understanding of a complex yet not fully understood etiology of these diseases, in particular diseases manifesting insulin resistance, and more particularly, moderate to severe insulin resistance, also iatrogenic insulin resistance.

Patients with insulin resistance are frequently afflicted with overt diabetes mellitus but may have normal tolerance to glucose. Indeed, a diverse array of clinical phenotypes have insulin resistance as a common element. As yet, there is no consensus molecular mechanism to explain the etiology of insulin resistance in the majority of these individuals. Among these various clinical syndromes, the degree of insulin resistance ranges from mild to severe. Essential hypertension is on the "mild" end of the insulin-resistance spectrum with insulin resistance increasing in severity from polycystic ovarian disease to the Type A syndrome to leprechaunism. The natural history of moderate to severe insulin resistance has not been studied in depth. The indications for treatment of hyperinsulinemia per se remain speculative. Moreover, there is no uniformly effective treatment for severe insulin resistance even in those patients with overt hyperglycemia. Indeed, over the last decade, investigators have learned more about the etiology of these conditions than about effective ways to treat them. Specific "complications" of insulin resistance ranging from hyperandrogenism and oligomenorrhea to hyperlipidemia usually are responsive to specific forms of therapy directed at these problems. Such forms of therapy are beyond the scope of this application. It remains uncertain whether therapies that reduce insulin resistance also will ameliorate the associated abnormalities.

Several therapies have been utilized for patients with severe insulin resistance. Attempts to treat severely affected patients may serve as a paradigm for the therapeutic approach to all patients with insulin resistance. In the past, the diversity and the rarity of patients with severe insulin resistance have made controlled trials with individual agents extremely difficult to perform. No large clinical trials with any agent have been reported. Most studies involve short trials of individual agents in single patients. The beneficial effects of any form of therapy is evaluated within the context of the underlying etiology and severity of the insulin resistance. It is clear that patients with congenital forms of severe insulin resistance are generally unresponsive to exogenous insulin unless massive doses are administered. In contrast, cases of acquired anti-insulin antibody mediated-insulin resistance have been reported to respond to sulfated insulin and U-500 porcine insulin. Additional strategies for the use of exogenous insulin in severely insulin resistant diabetic patients have been employed successfully.

More recently, recombinant human insulin like growth factor I (IGF-I) has become available. Clinical trials have been conducted to evaluate its effect in insulin resistant subjects.

INSULIN-LIKE GROWTH FACTORS

Insulin-like growth factors I and II are members of the proinsulin "superfamily". As their names imply, they share striking structural homology with proinsulin at the DNA and amino acid levels. Like proinsulin, and unlike insulin, IGF-I and IGF-II are single chain polypeptides of approximately 7400 MW. The homology between the IGFs and insulin extends beyond their structure. Both IGF-I and IGF-II bind to and activate the insulin receptor, although with a potency only 1–5% that of insulin itself. Thus, both IGF-I and IGF-II can stimulate "insulin-like" biological effects through the insulin receptor when present in sufficiently high concentrations.

IGF-I and IGF-II each bind to specific, high-affinity receptors that are distinct from one another. Each ligand binds to the receptor for the other ligand, although with significantly lower affinity. The structural homology between insulin and IGF-I continues to their receptors. The IGF-I receptor (type I receptor) is highly homologous to the insulin receptor. Both are heterotetramers comprised of 2 $\alpha$ and 2 $\beta$ subunits. The $\alpha$ subunits contain the ligand binding domain. The $\alpha$ subunit of the IGF-I receptor determines the high affinity binding for IGF-I, while the $\alpha$ subunit of the insulin receptor does the same for insulin. Chimeric receptors containing individual domains of the $\alpha$ subunits of the insulin and the IGF-I receptors can be constructed that retain high affinity binding for both ligands. The $\beta$ subunit of the IGF-I receptor, like that of the insulin receptor, has intrinsic tyrosine kinase activity that is activated by the binding of the ligand to the extracellular domain of the receptor. Both the insulin and IGF-I receptors utilize at least one common intracellular phosphotyrosine acceptor protein, IRS-1. Data from in vitro studies demonstrate that the type I IGF receptor can mediate IGF-I-stimulated increases in glucose transport.

The IGF-II receptor differs dramatically from the IGF-I and insulin receptors. Controversy over the role of the IGF-II receptor in signaling transmembrane events remains. The type II IGF-I receptor is the same receptor as the cation-independent mannose-6-phosphate receptor, a protein involved in intracellular transport events. Type II IGF receptor is a transmembrane protein and "free" extracellular domains are found in the circulation. IGF-I has an affinity for the type II IGF receptor approximately 5–10% that of IGF-II itself. Insulin has no appreciable affinity for the IGF-II receptor, while IGF-II binds with higher affinity to the insulin receptor than does IGF-I.

The IGFs differ structurally from insulin in one major respect. Both IGFs bind with variable affinity to at least six distinct binding proteins of molecular weight ranging from 23,000 to 180,000. Insulin does not interact with any of these binding proteins. The transcription rate and blood levels of IGF binding proteins are regulated by a complex series of hormones and nutritional factors, including growth hormone and insulin. IGF binding proteins serve both to prolong the plasma half-life of IGFs themselves, and to "control" free IGF levels. Since it is assumed that the free levels of IGF determine its metabolic effects, the IGF binding proteins (BP) both serve as a reservoir for IGF in the circulation and limit IGF availability to peripheral tissues. Specifically, IGF BPs have been demonstrated to decrease IGF-I stimulated glucose uptake and other IGF biological effects. Endogenous IGF binding proteins potentially are important modulators of the metabolic effects of exogenous IGFs in vivo.

The characteristics of IGFs offer a rationale for its use in patients with insulin resistance. IGF-I is an insulin analog with direct effects on glucose uptake through the IGF-I receptor in addition to its effects on protein metabolism and DNA synthesis. A number of studies in normal men have demonstrated that bolus administration of IGF-I administered either intravenously or by subcutaneous injection lowers blood glucose concentration with a kinetic pattern similar to that of insulin but with lower potency. Studies in rats and in dogs demonstrate that IGF-I is less potent than insulin in inhibiting hepatic glucose output compared to its ability to stimulate glucose uptake in peripheral tissues. Data in man do not show the same degree of differential effects. Intravenous infusion of IGF-I lowers insulin and C-peptide levels while maintaining normal glucose tolerance during either an OGTT or a mixed meal in normal volunteers. Part of the effect of IGF-I to inhibit insulin release is a direct effect on the β cell and is independent of blood glucose concentration. Thus, IGF-I is "insulin sparing" both through its ability to directly lower blood glucose concentration (and the "need" for endogenous insulin) and through its direct effects on β cell insulin secretion.

Euglycemic clamp studies in normal volunteers have demonstrated that IGF-I has a potency for stimulating glucose disposal approximately 7% that of insulin. Since the IGF-I receptor mediates the same spectrum of biological effects as the insulin receptor, it is possible that in some patients with insulin resistance involving defects at or just beyond the level of the insulin receptor, IGF-I will "bypass" such defects by using an alternative but functionally similar receptor. This possibility assumes that the IGF-I receptor is unaffected by the underlying genetic or metabolic process affecting the insulin receptor. Since the interdependence of the insulin and IGF-I receptors in mediating glucose homeostasis has not been elucidated fully, one might expect a spectrum of responses to IGF-I in patients with insulin resistance. Indeed, there already are two conflicting reports in murine models of diabetes. One model demonstrates the preservation of IGF-I sensitivity in the presence of insulin resistance while the other model demonstrates resistance to both insulin and IGF-I.

In addition, IGF-I lowers plasma triglycerides and LDL cholesterol and raises HDL cholesterol. Thus, IGF-I would be predicted to not only lower blood glucose and lower plasma insulin, but also to improve the lipid profile in at least some subjects with insulin resistance. It is not known what effect IGF-I might have on some of the phenotypic abnormalities associated with severe insulin resistance. Activation of the type I IGF receptor by high levels of insulin has been postulated to potentially contribute to both acanthosis nigricans and ovarian hyperandrogenism in subjects with severe insulin resistance. Thus, IGF-I therapy either may improve or worsen these abnormalities in the setting of severe insulin resistance.

To date, studies to determine a therapeutic basis for treatment of insulin resistance have varying results.

Instructive background information can be found in the following:

Elahi, D. et al., "Hemodynamic and metabolic responses to human insulin-like growth factor-1 (IGF-1) in men". In: *Modern Concepts of Insulin-Like Growth Factors*, (Spencer, EM, ed), Elsevier, N.Y., pp. 219–224, 1991.

Quinn, J. D. et al., "Acute response to recombinant insulin-like growth factor 1 in a patient with Mendenhall's syndrome". *N Engl J Med* 323(20):1425–1426, 1990.

Schalch, D. S. et al., "Short-term metabolic effects of recombinant human insulin-like growth factor 1 (rhIGF-1) in type 11 diabetes mellitus". In: *Modern Concepts of Insulin-Like Growth Factors*, (Spencer, EM, ed), Elsevier, N.Y., pp. 705–714, 1991.

Schoenle, E. J. et al., "Recombinant human insulin-like growth factor-1 (rhIGF-1) reduces hyperglycemia in patients with extreme insulin resistance". *Diabetologia*, 34 (9): 675–679, 1991.

Usala, A. L. et al., "Brief Report: treatment of insulin resistant diabetic ketoacidosis with insulin-like growth factor-1 in an adolescent with insulin-dependent diabetes". *N Engl J Med* 327: 853–857, 1992.

Zenobi, P. D. et al., "Metabolic Effects of recombinant human insulin-like growth factor 1 (rhIGF-1) in non-insulin dependent diabetes mellitus". *Program and Abstracts of the 73rd Annual Endocrine Society Meeting*, Washington, D.C., 1991, abstract 784, p. 226 later more completely disclosed in "Insulin-like Growth Facotr-I Improves Glucose and Lipid Metabloism in Type 2 Diabetes Mellitus" *J. Clin. Invest.*, Vol. 90, 2234–2241, December 1992.

Zenobi, P. D. et al., "Effects of Insulin-like growth factor-1 on glucose tolerance, insulin levels, and insulin secretion". *J Clin Invest* 89:1908–1913, 1992.

U.S. Pat. No. 4,988,675 issued on Jan. 29, 1991 to Froesch et al., "Method for Preventing Secondary Effects".

These references suggest a general scheme for the etiology of some clinical phenotypes which give rise to insulin resistance and the possible effects of administration of IGF-I to selected representative subjects. Of these studies, the teachings of which are incorporated herein by reference, several preliminary studies demonstrate that IGF-I can lower blood glucose concentrations in human subjects with NIDDM who have mild to moderate degrees of insulin resistance (Schalch, et al and Zenobi, et al) . Although study design varied, two of the studies demonstrated that IGF-I lowered both fasting and postprandial blood glucose concentration. In addition, it was found that IGF-I therapy reduced plasma LDL cholesterol levels. IGF-I also lowered blood glucose and plasma insulin levels in some individuals with severe insulin resistance. In Schoenle et al. the authors demonstrated the acute effect of intravenous IGF-I (100 μg/kg given as a bolus injection) in three subjects with the Type A syndrome of insulin resistance. In all three cases, the first injection of IGF-I lowered blood glucose slightly, but a second injection 2 hours later enhanced the effect. Concomitant with the decrease in blood glucose concentration, there was a dramatic decrease in plasma insulin and C peptide concentrations. The exact biochemical mechanism underlying insulin resistance in the three subjects studied is unknown. Further, there was also no quantitation of the degree of insulin resistance although all three subjects were noted to have a subnormal response to bolus intravenous insulin. The Rabson-Mendenhall syndrome presents an unusual phenotype associated with severe insulin resistance. In one subject with Rabson-Mendenhall Syndrome, an acute intravenous bolus of IGF-I significantly lowered blood glucose and plasma insulin concentrations.

Usala et al. recently reported an unusual patient with insulin-dependent (Type 1) diabetes mellitus and severe, intermittent insulin resistance that resulted in diabetic ketoacidosis. In Usala et al., intravenous bolus administration of IGF-I at a dose of 500 μg/kg reversed the hyperglycemia, reversed ketoacidosis, and lowered subsequent insulin requirements for several weeks. In fact, the patient responded to several courses of IGF-I therapy. The etiology of the insulin resistance in this patient is not known. These doses of intravenous IGF-I have not been used in other studies.

Thus, from the standpoint of efficacy, IGF-I shows some promise as an agent that will improve both glucose tolerance and hyperinsulinemia. At present, the specific clinical syndromes that respond to IGF-I have not been defined clearly. It is possible that response or lack of response to IGF-I administration may help to clarify the biochemical etiology of the insulin resistance. In addition, if IGF-I therapy can lower plasma insulin levels sufficiently, its use in patients with severe insulin resistance may clarify the relationship between hyperinsulinemia and some of the clinical and biochemical abnormalities associated with severe insulin resistance including the acanthosis nigrans and hyperandrogenism. Notwithstanding the positive indications, caution must be exercised in the use of IGF-I because activation of the type I IGF receptor by insulin potentially contributes to acanthosis and ovarian hyperadrogenism in subjects with severe insulin resistance. Thus, IGF-I may worsen these abnormalities and, accordingly, be contraindicated.

It is known that structural mutations within the insulin receptor gene represent the underlying abnormality in some individuals with severe insulin resistance. The basis of severe insulin resistance in other subjects remains undefined but appears not to be related to structural defects in either the insulin receptor or in the insulin-dependent glucose transporter (GLUT 4). The marked phenotypic heterogeneity of patients with severe insulin resistance and the presence of a subgroup of severely insulin resistant patients with "acromegaloid" features suggests a spectrum of biological effects in these individuals mediated by insulin and/or by insulin-like growth factor-I, polypeptides that share significant structural and functional homology.

The applicant has undertaken studies involving severely insulin-resistant individuals in order to further understand the relationship between the receptor defect and the phenotype.

The challenge in designing studies involving insulin resistance is that the ability of the insulin receptor both to bind and to be activated by IGF-I may be enhanced, diminished, or unaffected in individuals with known or presumed insulin receptor mutations. Alternatively, in individual whose insulin receptors are defective, the metabolic effects of IGF-I, acting through the type I IGF receptor, may have greater physiologic significance than in "normal" individuals.

By comparing the effects of IGF-I to the effects of insulin in severely insulin-resistant individuals and by comparing IGF-I's effects in individuals with known insulin-receptor mutations to its effects in those individuals whose receptor mutations have not yet been characterized, it is possible to (i) gain further information about the physiologic consequences of the specific defects in individuals with different clinical phenotypes associated with severe insulin resistance including those with and without known structural mutations in the insulin receptor; (ii) enhance understanding of the effects of IGF-I on glucose metabolism, lipid metabolism, ovarian androgen production and other processes, as well as its mechanism and site of action, (i.e., the insulin receptor or the IGF-I receptor) in both normal volunteers and in subjects with severe insulin resistance; (iii) assess the therapeutic efficacy of IGF-I, in terms of glucose metabolism, body composition, androgen metabolism, and other metabolic parameters, in individuals with severe insulin resistance.

Some subjects with severe insulin resistance have signs or symptoms that are associated with very high circulating insulin levels. These signs and/or symptoms include: the skin lesion acanthosis nigricans, ovarian hyperandrogenism, muscle hypertrophy, muscle cramps, hirsutism, irregular menses and lipodystrophy. Some of these subjects have mild to moderate hyperglycemia (elevated blood glucose concentrations). The severe insulin resistance that is present in these individuals means that insulin is not an effective form of treatment for hyperglycemia and that insulin will not reverse and may worsen some of the associated findings. It is possible that treatment with rhIGF-I will improve or reduce elevated blood glucose concentrations, if present, or that it may improve the acanthosis nigricans, muscle cramps, or hyperandrogenism.

Experience with recombinant human insulin-like growth factor is relatively limited. Studies suggest that rhIGF-I might possibly be used in rare patients with severe insulin resistance and diabetic ketoacidosis, in subjects with severe insulin resistance second to the Rabson-Mendenhall syndrome, in one subject with the rare genetic syndrome of leprechaunism and in several subjects with growth hormone resistance syndrome (Laron dwarfism). Since rhIGF-I is capable of lowering blood glucose concentration, there is the risk that subjects will develop hypoglycemia. RhIGF-I also has been associated with the development of jaw pain in a significant percentage of subjects who receive it sometimes requiring discontinuation of the drug. Postural hypotension has been reported rarely in subjects receiving IGF-I. RhIGF-I also has been associated with some edema in obese patients with type II diabetes mellitus.

No prior art is known which suggests safely treating disease by chronic modification of cell barrier properties by exposing the cell to a modification-effective amount of IGF-I for an exposure time of at least about 7 consecutive days, more particularly between about 14 days and about 31 days. Further, no prior art suggests a method of chronic amelioration of insulin resistance in a subject by exposing the patient to a modification-effective amount of rhIGF-I nor diagnosing or screening for rhIGF-I sensitive cell barrier properties.

SUMMARY OF THE INVENTION

A method of chronic modification of cell barrier properties by exposing the cell to a modification-effective amount of IGF-I for at least about 7 days is disclosed, more particularly, wherein the modification effective amount is between about 50 μg/kg and less than about 500 μg/kg, more particularly, less than about 24 μg/kg/hr or less than about 288 μg/kg in a 12 hour period, even more particularly, about 100 μg/kg body weight twice daily. In one embodiment involving animals, any mode of administration known in the art can be used such as but not limited to, intravenously, intramuscularly, orally, parenterally, or enterally, although subcutaneously is preferred. The method of the instant invention can be performed via in vivo treatment of humans in need of such treatment. In other embodiments, particularly in in vitro embodiments, an effective dose is about 0.5 ng/ml to about 1 mg/ml of presented drug concentration of the medium in which the cells are presented, such as but not limited to, blood, serum, Ringer's lactate, blood agar and other similar media. Still further, the instant invention discloses a method of chronic amelioration of insulin resistance in a patient by exposing the patient to a modification-effective amount of rhIGF-I for an exposure time of at least about 7 consecutive days. Also, a method of diagnosing rhIGF-I sensitive cell barrier properties comprising by quantifying native-state cell barrier properties, exposing cells to a modification-effective range of rhIGF-I then challenging the exposed cell to determine a change in the cell barrier properties is disclosed. The instant invention also discloses a method of chronic reversal of insulin resistance in human with severe insulin resistance by administering rhIGF-I in a dose of 100 μg/kg body weight subcutaneously twice a day for about 21 consecutive days to about 28 consecutive days, and in particular, about 22 to about 24 consecutive days. Once the period of administration is complete, a subject maintains the reversal for a period of about 28 days before beginning a decline which ultimately places the subject at pre-treatment levels necessitating a repeat of the IGF therapy.

DETAILED DESCRIPTION

In the course of clinical trials designed by the applicant to evaluate the effects of recombinant human insulin-like growth factor I (IGF-I) on glucose metabolism and insulin sensitivity, it was discovered that certain dosages, formerly considered ineffective could produce surprising results which have implications for the use of IGF-I in human disease. The present invention discloses a general method of modifying cell barrier properties in such a way that, among other things, severe insulin resistance is reversed for a period of time.

The advantages to the present invention are numerous, however, a particular advantage is the safety of low dosages which previously have been shown to be ineffective or minimally effective for example in Schoenle et al where a dose of 100μg/kg had a minimal effect. With the method of the instant invention, intermittent therapy is possible thereby reducing the risk of potential drug complications and the expense of the therapy. Further, once the modification occurs, it can be sustained over a period of time before resuming treatment.

DEFINITIONS

For purposes of this application the following definitions shall be used:

Animal shall mean mammals including humans.

Cell barrier properties shall mean a system for regulating the surface/exterior, surface/interior and transmembrane interactions including components of active transport and/or binding proteins, such as postulated pumps, for example, a sodium pump, gates, receptors, energy transducers or enzyme/complement-type dynamic associations which facilitate and control the entry, exit and attachment of chemicals such as, but not limited to, glucose, endogenous insulin, exogenous insulin, C-peptides, proinsulin, glucagon, triglycerides, insulin-like growth factor-I and -II, recombinant human insulin-like growth factor-I and -II, and growth hormones.

Chronic shall mean between about 7 days to about 60 days, more particularly, 14 days to 22 days, even more particularly between about 21 days and 31 days.

IGF shall mean Insulin-like growth factor, analogs and derivatives thereof, more particularly, Insulin-like growth factor-I (IGF-I) and -II (IGF-II), even more particularly, recombinant human Insulin-like growth factor-I (rhIGF-I), without diminishing the generality of these terms, "analog" shall mean chemical compounds which are similar in structure to IGF and "derivatives" shall mean substances and the compounds formed therefrom by simple chemical processes in which "skeleton" of IGF still exists.

Iatrogenic insulin resistance shall mean insulin resistance developed as a complication because of treatment for another disease, such as but not limited to, steroid glucocorticoid (Cushing's syndrome), acromegaly, and obesity.

Insulin resistance shall mean high blood glucose levels, markedly elevated serum insulin concentrations, insensitivity to intravenously administered insulin.

Modification-effective amount shall mean a range of dosages below the maximum tolerated dose (MTD), in some embodiments the pharmacologically acceptable dose is between about 50 μg/kg and less than about 500 μg/kg, in some other embodiments the dose is less than about 24 μg/kg/hr or less than about 288 μg/kg in a 12 hour period, in still other embodiments the dose is about 100 μg/kg body weight twice daily, administered subcutaneously or its equivalent if administered intravenously, intramuscularly, orally, topically or any other pharmacologically mode of administration, in still other embodiments, particularly in vitro embodiments, the dose is about 0.5 ng/ml to about 1 mg/ml of presented drug concentration of the medium in which the cells are presented, such as but not limited to, blood, serum, Ringer's lactate, blood agar and other similar media.

Native state shall mean as found in nature and/or before treatment.

Severe insulin resistance shall mean a fasting plasma insulin of greater than 40 uU/ml (nl less than 15 uU/ml), a post-glucose insulin level of greater than 300 uU/ml at 60–180 minutes after glucose administration, and a decrement of blood glucose concentration of less than 50% following the intravenous administration of insulin at 0.6 U/kg body weight or in the absence of endogenous insulin the failure to have a decrement of blood glucose concentration of equal to or greater than 50% following the intravenous administration of insulin at 0.6 U/kg body weight.

BRIEF DESCRIPTION OF THE FIGURES

FIG. 7 further depicts blood glucose levels following a liquid mixed meal obtained 1 week and 3 weeks after the subject stopped taking rhIGF-I.

FIG. 9 depicts a flow sheet for practicing the protocol.

In one embodiment of the present invention human subjects were selected for severe insulin resistance. Each subject served as his/her own control. The majority of subjects were women as women are affected more commonly than men with severe insulin resistance. No effort was made to recruit subjects of a specific race, gender, or socioeconomic group. Subjects with severe insulin resistance are rare, accordingly the study population was non-uniform (not normally distributed). The acute response of individual subjects to insulin was compared before and after subcutaneous IGF-I twice daily for 4 weeks. Normal volunteers (non-insulin resistant, non-diabetic volunteers) were recruited to undergo the initial phase of the evaluation.

It has been found that some subjects with severe insulin resistance express specific mutations in the insulin receptor; other subjects have severe insulin resistance for unknown reasons. The subjects vary in the clinical manifestations of their insulin resistance and these manifestations range from the type A syndrome of insulin resistance to lipodystrophy to a condition which the applicants have termed "pseudoacromegaly".

Generally, subjects on whom the method of the instant invention is practiced are screened and studied with a variety of tests to assess their degree of insulin resistance. Subsequently, the subjects are administered a one-month course of subcutaneously administered IGF-I. Periodic safety assessments as well as repeat measurements of the degree of their insulin resistance and other metabolic parameters are performed. IGF-I doses begin at 100 µg/kg twice daily (BID) subcutaneously (SC) to test for tolerance and for efficacy although other dosages and modes of administration consistent with this disclosure are contemplated. If this initial dose is tolerated but if there is no evidence of beneficial response (decrease in blood glucose or plasma insulin) after 2–4 days of therapy, the dose can be increased to 150 µg/kg BID SC. The increased dose can be continued as long as fasting blood glucose remains above 120 mg/dl. In one embodiment such as the embodiment represented in Example 1, the maximum dose of IGF-I utilized was 10 mg SC BID or 100 µg/kg BID.

Figure 10:
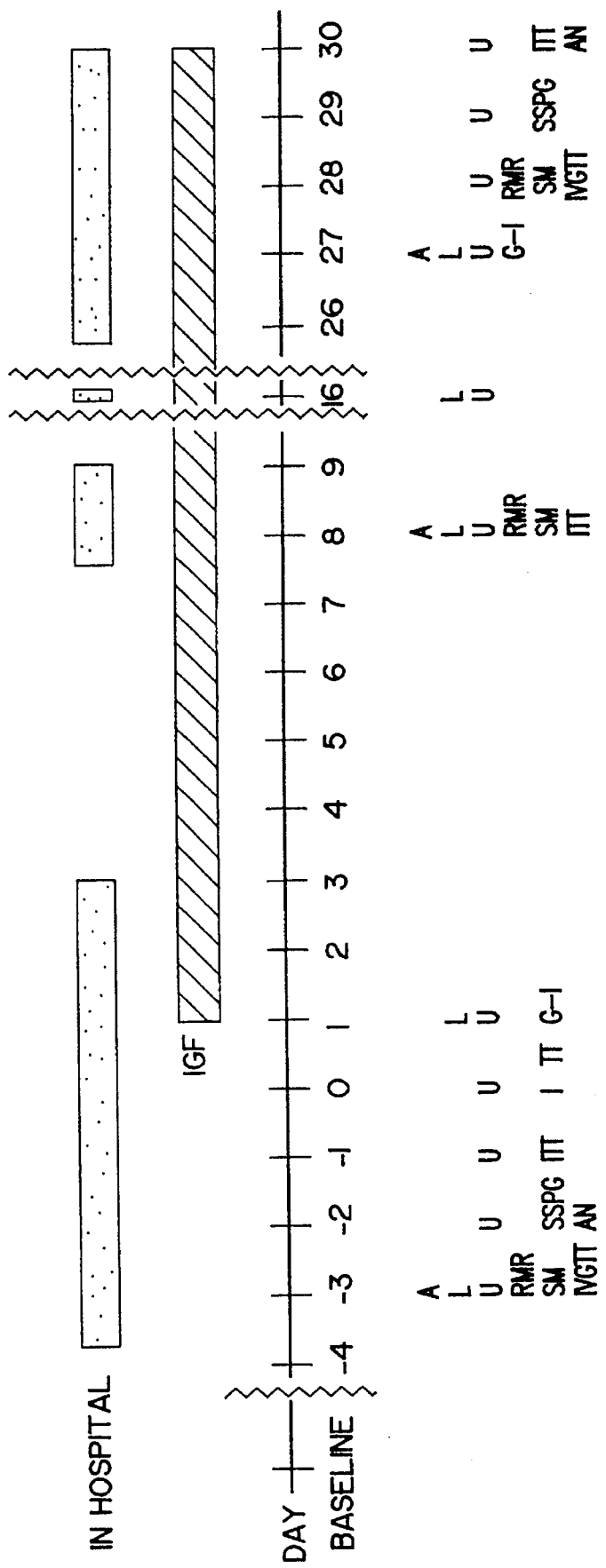
FIG. 10 depicts a schematic diagram of the study showing the particular monitoring tests performed on a particular day, and further showing the days of inpatient admission and the days on which the rhIGF-1 is administered. Day 1 is numbered as the day on which IGF-I is first administered to the subject.

A schematic diagram of one embodiment of the instant invention is shown on FIGS. 9 and 10 illustrating, among other things, approximate times for various preferred tests and procedures. In these figures, baseline screening is performed at −14 to −28 days (where Day 1 is the date of first administration). It is contemplated that this screening can be performed by phone and through discussions with the referring physicians of subject upon whom the method of the instant invention is practiced. It is expected that in many instances, the subject will be on insulin or oral hypoglycemic agents which must be discontinued with continued monitoring of blood glucose if clinically indicated. The vast majority of subjects are expected to have normal fasting blood glucose concentrations and thus not be on diabetic therapy.

One embodiment is described in Example 1, a complete history and physical examination must be performed. In carrying out the protocol, menstrual history of female participants are recorded. It is preferred that studies using the protocol carried out in the early follicular phase of the menstrual cycle if they are cycling normally. Initial laboratory evaluation must include a complete blood count, fasting glucose, electrolytes, BUN, creatinine, SGOT, SGPT, alkaline phosphatase, total bilirubin, urinalysis, EKG, and in women, B-HCG (to rule out pregnancy). A 40 gm/M$^2$ 3-hour oral glucose tolerance test with measurements of glucose, insulin and C-peptide, at times 0, 30, 60, 90, 120, and 180, also is performed to define the degree (if any) of glucose intolerance and the degree of insulin resistance as measured by peak serum insulin levels and the area under the plasma insulin/time curve. At present, the doses contemplated by the method of the instant invention have no known contraindications for any particular segment of the population. Thus, although certain subjects are ruled out for purposes of the study disclosed herein, treatment for insulin resistance using the method of the instant invention is appropriate for any person suffering from insulin resistance. All populations currently treated by alternative methods such as those set out in the Background would be ideal candidates for treatment using the method of the instant invention.

For purposes of the study conducted pursuant to the protocol (hereinafter referred to as "the study"), pregnancy in female subjects must be ruled out prior to entry into the study. Use of barrier contraceptive is advised to female subjects in the study. Further, female subjects using oral contraceptive agents must discontinue these medications 2 months prior to entry into the study as these agents may accentuate the degree of insulin resistance. In the rare subject on therapy for significant hyperglycemia (FBS >120 but <160 mg/dl), oral hypoglycemic agents and/or insulin must be discontinued at least 2 weeks prior to study, and glycemic control must be assessed by home glucose monitoring and outpatient visits. Subjects with significant hyperglycemia but who are poorly controlled on insulin or oral hypoglycemic agents must discontinue these agents at least 3 days prior to entry into the study.

Blood glucose concentrations must be monitored closely when subjects are first started on the rhIGF-I and doses must be adjusted to avoid hypoglycemia. It is important to note that subjects with GH resistance syndrome who are prone to hypoglycemia do not develop hypoglycemia on 100 µg/kg twice daily SC.

Similarly, it is contemplated that when practicing the method of the instant invention on the general population of persons in need of treatment, such as persons with severe insulin resistance, that IGF-I therapy be used alone. However, IGF-I therapy can be combined with administration of supplemental agents, such as insulin, which would enhance the response in an individual. Any of the agents such as those listed in the Background section could serve as a potential supplemental agent. Persons who are receiving therapy pursuant to the method of the instant invention must be initially assessed and monitored to determine the individuals tolerance for the therapy.

Both in the study and generally, it is contemplated that there be an initial assessment of metabolic status, insulin action, peripheral insulin resistance, glucose response to insulin at baseline. After beginning administration of IGF-I, usually about 6 days to about 10 days, more particularly 1 week, another assessment (short term assessment) is performed.

THE PROTOCOL

After the baseline screening and metabolic assessment described above has been performed, eligible subjects are admitted into a hospital for more complete metabolic characterization. The schedule depicted in FIGS. 9 and 10 is followed as closely as possible. Throughout the admission, all subjects follow a 4 gram sodium diet, with caloric intake calculated to allow maintenance of body weight. When not participating in a specific metabolic test, subjects remain on in the hospital, but allowed ad libitum activity.

Anthropometric Evaluation

If insulin sensitivity is dramatically improved after IGF-I administration, changes in body fat content or body fat distribution may occur. Thus, height, weight, waist and hip circumference, body composition by bioelectric impedance, and skin fold measurements are assessed on days −3, 8 and 27 (see FIG. 9). Since postural hypotension is a potential side-effect of IGF-I administration, and since hyperinsulinemia is associated with hypertension, postural blood pressure and pulse also must be measured.

Laboratory Evaluation

After an overnight fast on days −3, 1, 8, 16, and 27 (twice before IGF-I administration, and one week and four weeks after beginning IGF-I), extensive laboratory evaluation must be undertaken as part of the safety assessment and determination of biological effects of IGF-I administration. Electrolytes, BUN and creatinine are be measured for routine screening, and renal function is further monitored by 24 hour urinary creatine and protein measurements and assessment of creatinine clearance. Assessment of fasting glucose, fructosamine, insulin, growth hormone, IGF-I, and IGF-I binding proteins before and after short and longer term IGF-I administration provides important information about the effects of IGF-I in subjects enrolled in the study. Because IGF-I and insulin differentially regulate various IGF BPs, measurement of these binding proteins may provide further insight into the specific receptors utilized by insulin and IGF-I in these patients with severe insulin resistance. Because alterations in glycemic status occurring with IGF-I administration (and/or other direct effects of IGF-I) may alter lipid metabolism, and may effect sex steroids, HDL, LDL, total cholesterol and triglycerides, LH, FSH, 17-hydroxyprogesterone, DHEA-Sulfate, Sex Hormone Binding Globulin (SHBG), and total and free testosterone are measured.

Resting Metabolic Rate (RMR)

Since the hyperinsulinemia of insulin resistant states appears to be associated with increased RMR, and an improvement in insulin resistance after IGF-I administration in at least some of these subjects is anticipated, RMR is measured basally, after one week and four weeks of IGF-I therapy. Resting metabolic rate remains the best measure of basal metabolism in resting humans. Insulin induces an increase in metabolic rate in normal humans but neither resting nor insulin-induced changes in metabolic rate have been studied in subjects with severe insulin resistance. IGF-I may produce similar changes to metabolic rate in normal subjects as does insulin but it has not yet been tested systematically. Moreover, its effects on metabolic rate in subjects with severe insulin resistance are not known and may provide further clues to the mechanisms of action of IGF-I in these individuals.

After a 12 hour overnight fast, subjects are awakened, asked to void, and weighed in a hospital gown. Subjects remain at bedrest until completion of measurement of RMR over a 45 minute period. An open-circuit indirect calorimetry system with a transparent ventilated hood, ideally this is interfaced to a computer.

Sustacal Meal

Insulin response to secretogogues other than glucose does not necessarily correlate with the response to glucose. The effect of a standard mixed meal (carbohydrate, fat, and protein) on insulin secretion before, and after short and longer term IGF-I administration must be evaluated. By measuring C-peptide response, as well as glucose and insulin, an estimate of insulin secretion can be made despite high circulating insulin levels in subjects.

After an overnight fast, and after measurement of RMR as described above on days −3, 8, and 28, an indwelling venous catheter is placed in the forearm and blood is obtained for fasting blood glucose, insulin, and C-peptide as well as the other laboratory studies described above. Each subject is then given a standard breakfast of 250 cc of the dietary supplement Sustacal (which contains 45 g cho, 14.4 g protein, and 13.6 g fat, total kcal=360), and glucose, insulin, and C-peptide are measured at 30 minute intervals for a total of three hours.

Intravenous Glucose Tolerance Test

The bolus intravenous administration of glucose (0.50 gm/kg BW) provides a standard, controlled way to assess both pancreatic β-cell secretory capacity and peripheral glucose uptake in the whole organism. No systematic studies have been performed on insulin secretion (particularly 1st phase insulin secretion) in subjects with severe insulin resistance. No data are available on the effects of IGF-I administration on 1st and 2nd phase insulin secretion in such subjects.

Subjects are studied in the supine, resting state at 4:00 PM on days −3, 8, 27. An intravenous line is placed in a large forearm vein and kept patent with intravenous infusion of normal saline. A separate intravenous line will be started in the contralateral antecubital fossa and utilized for the bolus injection over 3 minutes of sufficient volume of 50% glucose solution to provide 0.50 gm glucose/kg body weight (up to 75 gm). Blood is sampled for insulin and glucose at −15, −10, −5, and 0 times and at +1, +3, +5, +10 and every 10 minutes thereafter for 90 minutes.

Steady State Plasma Glucose (SSPG)

A number of methodologies have been used to assess both peripheral and hepatic insulin action (and insulin resistance). While it generally is accepted that the euglycemic clamp is the most definitive of these methods, studies undertaken using this protocol utilize the SSPG method popularized by Reaven et al and well known to those skilled in the art. This method offers several advantages over other methods. First, it is far less intensive for the study subject than a clamp procedure, a particular advantage in the setting of an otherwise rigorous protocol. Second, the expense of the clamp procedure is high and each subject should be "clamped" both with insulin and IGF-I. Third, it is possible to define the presence of insulin resistance with an intravenous insulin tolerance test. Finally, if subjects also are resistant to insulin or if there is evidence from 24 hr urine collections or other data that the subjects respond to IGF-I in ways other than glucose metabolism, a clamp procedure can be performed later, after withdrawal of IGF-I for 2–4 weeks.

Following an overnight fast, an indwelling venous catheter is placed, an 30 minutes thereafter, basal blood samples is collected. Somatostatin is then administered as a 125µg bolus, followed by a constant infusion at 350 µg/hr. Alternatively, octreotide a synthetic analog of somatostatin currently used clinically can be administered as an intravenous bolus of 50 (fifty) µg followed by an infusion rate of 2.0 µg/kg/hr. Simultaneously, infusions of glucose at 6 mg/min/kg and insulin (U-100 regular human) at 0.77 mU/kg/min begin by continuous pump for 180 minutes. Blood samples for steady-state plasma glucose and insulin are obtained every half hour for the first 150 minutes, and then every 10 minutes for the last 30 minutes of the 3 hr infusion. In some subjects with severe insulin resistance, this test may need to be repeated at a higher insulin infusion rate because of their lack of response to the 0.77 mU/kg/min dose.

Intravenous Insulin Tolerance Test (ITT)

The ITT represents a simple and reproducible method for assessing insulin sensitivity in vivo. In these markedly insulin resistant individuals, the standard dose of insulin used in this protocol, 0.1–0.2 U/kg, results in plasma insulin levels within the range that these subjects generate postprandially, and will be unlikely to result in significant hypoglycemia. By repeating the test with incremental increases in the insulin dose, a determination of the amount of insulin needed to lower plasma glucose by 50% can be made and an insulin "dose-response" curve can be constructed. The ITT is performed on day −1 and again after one and four weeks of IGF-I administration, to allow an assessment of the effects of short (1 week) and longer (1 month) term IGF-I administration on this measure of insulin sensitivity.

After an overnight fast, an indwelling venous catheter is placed in the forearm, and 0.15 U/kg of U-100 human regular insulin is injected intravenously as a rapid bolus. For normal volunteers, the initial dose of insulin is 0.5 U/kg body weight. The plasma glucose is then measured at 10 minute intervals for the next 60 minutes. If plasma glucose drops to 50% of the starting value, or less than 50 mg/dl, the test is terminated. If plasma glucose drops by 25% or less, the insulin dose will be doubled, and plasma glucose measured as described above. If plasma glucose drops by more than 25%, but less than 50% (and the absolute value is greater than 50 mg/dl) after the first dose of insulin, the dose is increased to 1.5 times the initial dose, and glucoses sampled as described. This procedure is repeated until a 50% decrement in plasma glucose (or an absolute value of 50 mg/dl or less) is achieved or until a dose of 2.4 U/kg has been administered without a lowering of blood glucose by 50%. If symptomatic hypoglycemia develops, the test will be terminated and the subject treated with oral or intravenous glucose if the symptoms include those associated with neuroglycopenia (confusion, decreased level of consciousness). Glucose will then continue to be monitored at 10 minute intervals for an additional 30 minutes or until symptoms resolve or blood glucose is greater than 60 mg/dl.

Frequent Glucose, Insulin and C-peptide Sampling (G-I)

IGF-I is administered at a dose of 100 µg/kg BID subcutaneously from day 1 to day 30. This dose has been tolerated by normal subjects and individuals with the growth hormone resistance syndrome (Laron dwarfism) without hypoglycemia. Frequent measurements of glucose, insulin and C-peptide on day 1 and day 27 of IGF-I administration has several purposes: i) to assure the safety of subcutaneous IGF-I administration, since the degree of hypoglycemia occurring in response to IGF-I in these subjects is unknown; ii) to provide another measure of the effect of IGF-I on insulin sensitivity by comparing plasma insulin levels before, acutely after the start of IGF-I administration, and after 4 weeks of IGF-I; and iii) to assess the degree of suppression of endogenous insulin production (as indicated by the ratio of C-peptide to insulin) occurring acutely and after 4 weeks of IGF-I administration.

After an overnight fast, an indwelling venous catheter is placed in the forearm, and a fasting sample for glucose, insulin, and C-peptide will be obtained at 7:00 AM. The subject then follows the previously described diet, with meal times fixed at 8:00 AM, 12:00 PM, and 6:00 PM, and snacks at 4:00 PM and 10:00 PM. The subject is confined to the hospital, but allowed ad libitum activity. Blood samples for glucose, insulin and C-peptide are taken hourly. Subcutaneous administration of IGF-I commences just after the 4:00 PM blood sample. Hourly sampling continues through 4:00 PM on day 2. After readmission to the hospital on day 27, the subject continues to receive subcutaneous IGF-I as outlined above, again fasts overnight and follows the fixed meal schedule outlined above. An indwelling venous catheter is placed for hourly sampling from 7:00 AM to 4:00 PM.

Measurement of acanthosis nigricans

Acanthosis nigricans (AN) is an associated finding in the majority of subjects with severe insulin resistance. The mechanisms underlying the development of these lesions which often are quite disfiguring for the patients are not known but the lesions appear to be ameliorated as serum insulin levels fall. The role of IGF-I in producing or maintaining these lesions is not clear although anecdotal evidence suggests that IGF-I may reduce the degree and severity of acanthosis nigricans.

Subjects with visible AN are photographed at entry into the study with particular attention being placed on recording areas affected with acanthose nigricans. Three millimeter punch skin biopsies will be obtained from 2 different sites where possible from each subject with AN prior to initiating the trial of SC IGF-I. Photographs and biopsies are be repeated at day 27 of the study.

One preferred schedule is as follows although adjustments must be made for the particular circumstances of each subject:

Day −4: (Inpatient Day 1) A subject is admitted to hospital where a history and physical examination is performed. The subject is placed on a weight maintaining house diet and allowed ad libitum activity while in the hospital.

Day −3: (Inpatient Day 2) The subject undergoes anthropometric evaluation, laboratory evaluation, 24 hour urine testing and resting metabolic rate analyses. The subject then eats a Sustacal meal in the morning. In the afternoon, an intravenous glucose tolerance test (IGTT) is performed.

Day −2: (Inpatient Day 3) The subject undergoes 24 hour urine collections and a steady state plasma glucose (SSPG) is drawn.

Day −1: (Inpatient Day 4) The subject continues the 24 hour urine collections and a stepped dose insulin tolerance test (ITT) is performed.

Day 0: (Inpatient Day 5) The subject continues the 24 hour urine collection and the stepped dose insulin tolerance test (ITT) is continued.

Day 1: (Inpatient Day 6) The IGF-I therapy is administered to the subject at 100 µg/kg BID SC. The subject's blood and urine are monitored with glucose and insulin levels are drawn frequently.

Day 2: (Inpatient Day 7) IGF-I is administered. An assessment is then taken of the subject for any medical symptoms suggesting that continuing with the therapy is contraindicated. The 24 hour urine collections continues for analysis.

Day 3: The subject is discharged from the hospital and instructed to return for outpatient follow-up visits. For four days, the subject continues to receive IGF-I SC BID.

Day 7: (Inpatient Day 8) The subject returns to the hospital and is admitted for further therapy. Upon admission, a patient history and physical examination is performed to determine the subject's medical condition since discharge.

Day 8: (Inpatient Day 9) A repeat of the Protocol of Day −3 is performed, except that ITT is performed instead of IVGTT.

Day 9: The subject is discharged from the hospital.

Day 19: The subject returns for an outpatient visit where a brief patient history and physical examination is performed to assess the patient's condition since discharge. An interval laboratory evaluation and 24 hour urine collection is performed.

Day 26: (Inpatient Day 10) The subject is re-admitted to the hospital. Interval history and physical examinations are performed.

Day 27: (Inpatient Day 11) Anthropometric measurements are taken. Laboratory evaluation is performed. 24 hour urine collection and frequent insulin-glucose measurements are taken.

Day 28: (Inpatient Day 12) 24 hour urine is taken as well as resting metabolic rate. The subject eats a Sustacal meal followed by an intravenous glucose tolerance test.

Day 29: (Inpatient Day 13) 24 hour urine is taken. Steady state plasma glucose (SSPG) is performed.

Day 30: 24 hour urine is taken. Intravenous insulin tolerance test is performed. IGF-I is discontinued. The subject is discharged from the hospital.

The sequence is not always critical thus variations in the schedule are acceptable within reasonable bounds.

It should be noted that a subject at another center who received intravenous IGF-I at a dose of 34 µg/kg/hr developed an 11 second episode of asystole within 10 minutes of the start of infusion. The subject recovered spontaneously and had no long-term complications from this study. For this reason and because this side-effect was felt to be secondary to intravenous IGF-I administration, it is preferred that there be no intravenous infusion or bolus administration in this protocol. There is no evidence that subcutaneous IGF-I administration is associated with cardiac rhythm disturbances.

The study undertaken pursuant to the protocol involved the determination of sensitivity of human subjects to insulin and to IGF-I. Another caution in practicing the protocol is that part of the testing requires the induction of hypoglycemia. Such testing rarely can be associated with loss of consciousness or seizures but this testing (with insulin) is a routine part of the evaluation of pituitary function in patients with suspected hypopituitarism or with isolated growth hormone deficiency. Subjects must be monitored at the bedside with frequent (every 10 minutes) blood glucose measurements. Intravenous glucose solution will be available at the bedside to rapidly reverse many symptomatic hypoglycemia if it occurs. As with any study that involves multiple blood drawings and intravenous infusions, there is a small risk of bruising of the skin or of infection at the site of intravenous lines. Standard precautions must be taken to avoid these potential risks.

The protocol is instructive regarding the potential risks associated with administration of IGF-I to humans. It is contemplated that all similar tests should be run on the subject receiving an initial course of treatment under the method of the instant invention, including but not limited to, pre-administration baselines and repeated within the first 24 hours after injection. Once the subject's tolerance is established, the extensive tests need not be repeated for subsequent courses of treatment unless the subject complains or exhibits symptoms as outlined herein.

The compositions of this invention possess valuable pharmacological properties. They normalize blood glucose concentration, reverse insulin resistance, and reverse hyperinsulinemia in human and veterinary medicine. This effect can be demonstrated, for example, using the method of administering rhIGF-I in a dose of 100 µg/kg body weight subcutaneously twice a day for about 21 consecutive days to about 28 consecutive days.

Thus, these compositions can be used to treat subjects exhibiting high blood glucose levels, markedly elevated serum insulin concentrations, insensitivity to intravenously administered insulin and/or evidence of insulin receptor antibodies, more particularly, insulin resistant subjects.

The compositions are particularly useful in reversing insulin resistance, more particularly hyperinsulinemia, even more particularly patients with type A syndrome of insulin resistance, Rabson-Mendenhall syndrome, severe insulin resistance complicating type I diabetes mellitus, type II diabetes, and iatrogenic insulin resistance.

In addition, the compositions can be used in in vitro diagnostics and screening to determine sensitivity of a subject to rhIGF-I.

The compositions of this invention are generally administered to animals, including but not limited to mammals including humans. The pharmacologically active compositions of this invention can be processed in accordance with conventional methods of Galenic pharmacy to produce medicinal agents for administration to patients, e.g., mammals including humans.

The compositions of this invention can be employed in admixture with conventional excipients, i.e., pharmaceutically acceptable organic or inorganic carrier substances suitable for parenteral, enteral (e.g., oral or inhalation) or topical application which do not deleteriously react with the active compositions. Suitable pharmaceutically acceptable carriers include but are not limited to water, salt solutions, alcohols, gum arabic, vegetable oils, benzyl alcohols, polyethylene glycols, gelatin, carbohydrates such as lactose, amylose or starch, magnesium stearate, talc, silicic acid, viscous paraffin, perfume oil, fatty acid esters, hydroxy methylcellulose, polyvinyl pyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compositions. They can also be combined where desired with other active agents, e.g., vitamins.

For parenteral application, particularly suitable are injectable, sterile solutions, preferably oily or aqueous solutions, as well as suspensions, emulsions, or implants. Ampoules are convenient unit dosages. Also for parenteral application, particularly suitable are tablets, dragees, liquids, drops, suppositories, or capsules. A syrup, elixir, or the like can be used wherein a sweetened vehicle is employed.

Sustained or directed release compositions can be formulated, e.g., liposomes or those wherein the active component is protected with differentially degradable coatings, e.g., by microencapsulation, multiple coatings, etc. It is also possible to freeze-dry the new compositions and use the lyophilizates obtained, for example, for the preparation of products for injection.

Administration by injection, e.g. subcutaneous, intramuscular or constant infusion by intravenous drip is preferred. Additionally, a transmembrane administration, for example, a transdermal patch would be a particularly effective form of administration because the doses are relatively low and the administration must occur over a long period of time, that is, between about 7 and 30 days.

Generally, the compositions of this invention are dispensed in unit dosage form comprising about 50 to about 150 μg/kg in a pharmaceutically acceptable carrier per unit dosage.

For topical application, there are employed as nonsprayable forms, viscous to semi-solid or solid forms comprising a carrier compatible with topical application and having a dynamic viscosity preferably greater than water. Suitable formulations include but are not limited to solutions, suspensions, emulsions, etc., which are, if desired, sterilized or mixed with auxiliary agents, e.g., preservatives, stabilizers, wetting agents, buffers or salts for influencing osmotic pressure, etc. For topical application, also suitable are sprayable aerosol preparations wherein the active ingredient, preferably in combination with a solid or liquid inert carrier material, is packaged in a squeeze bottle or in admixture with a pressurized volatile, normally gaseous propellant, e.g., a freon.

The dosage of the compositions according to this invention generally are between about 50 μg/kg and less than about 500 μg/kg, more particularly, less than about 24 μg/kg/hr or less than about 288 μg/kg in a 12 hour period, preferably, about 100 μg/kg twice daily for at least 21 days when administered to treat insulin resistance, in particular, severe insulin resistance. In in vitro embodiments, the acceptable dose is about 0.5 ng/ml to about 1 mg/ml of presented drug concentration of the medium in which the cells are presented, such as but not limited to, blood, serum, Ringer's lactate, blood agar and other similar media.

It will be appreciated that the actual preferred amounts of active compositions in a specific case will vary according to the specific compositions being utilized, the particular compositions formulated, the mode of application, and the particular situs and organism being treated. Dosages for a given host can be determined using conventional considerations, e.g., by customary comparison of the differential activities of the subject compositions and of a known agent, e.g., by means of an appropriate, conventional pharmacological protocol.

EXAMPLE 1

A first human subject (Subject 1) with severe insulin resistance was enrolled in a protocol to test the effectiveness of IGF-I. All use of insulin or oral hypoglycemic agents was discontinued prior to the start of the below-described protocol. This subject received therapy for 22 consecutive days. The protocol listed above was followed.

Figure 1:
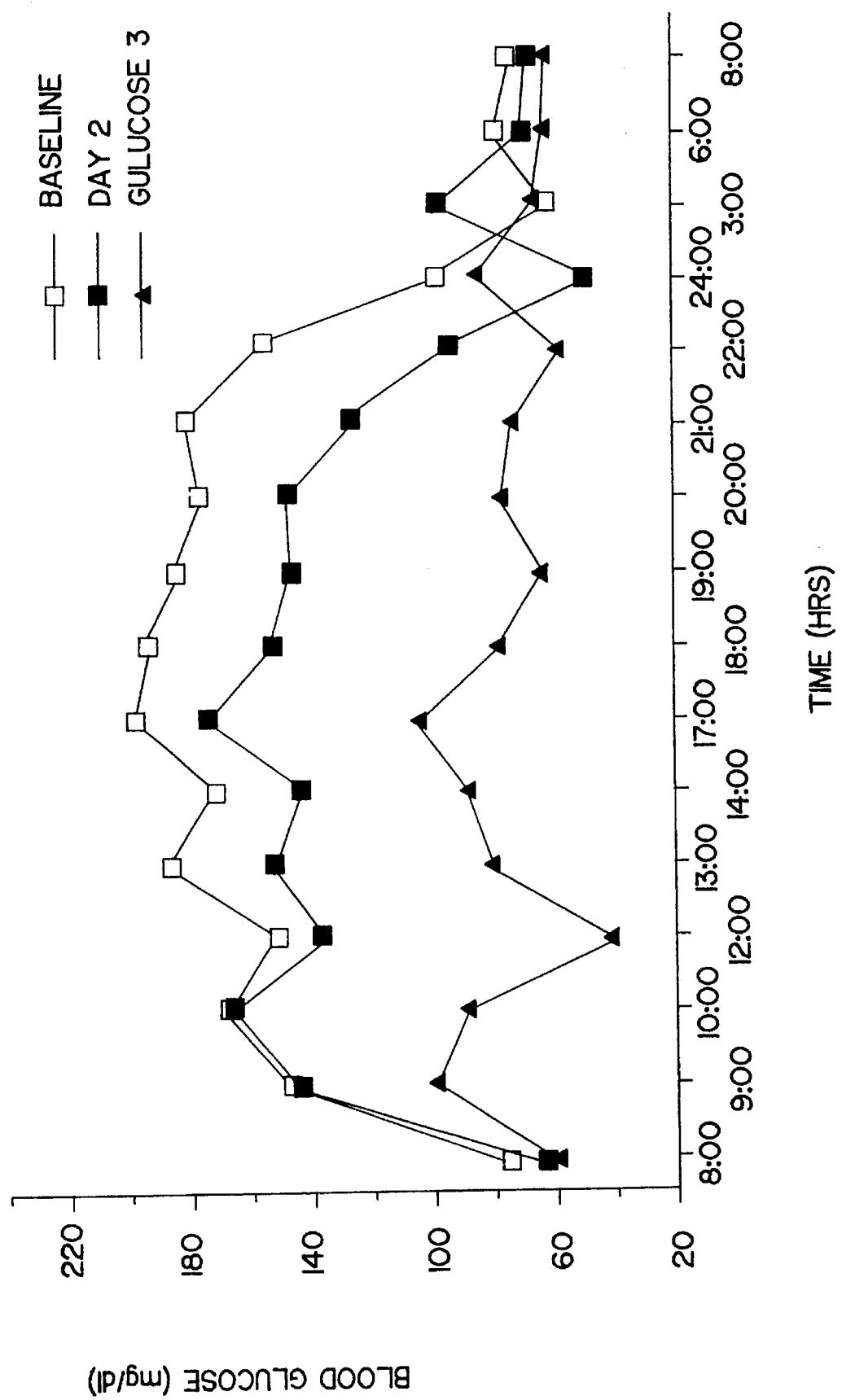
FIG. 1 depicts the effects of rhIGF-1 on blood glucose excursion following 3 mixed meals and 2 snacks in a human subject with severe insulin resistance.

FIG. 1 depicts the effects of rhIGF-I on blood glucose excursion following 3 mixed meals and 2 snacks in subject 1. Baseline data reflect blood glucose concentrations prior to therapy with IGF-I. Day 2 reflects data collected on the 2nd day of IGF-I administration (dose #2 and dose #3 administered at 8 AM and 5 PM respectively). Glucose 3 represents data collected on the 22nd day of IGF-I administration with dosing of 100 μg/kg s.c. BID at 8 AM and 5 PM. The data reveals that IGF-I improved glucose excursions slightly within 36 hours of initiating therapy and reversed glucose intolerance by 3 weeks of therapy. This time dependent effect had not been observed previously.

Figure 2:
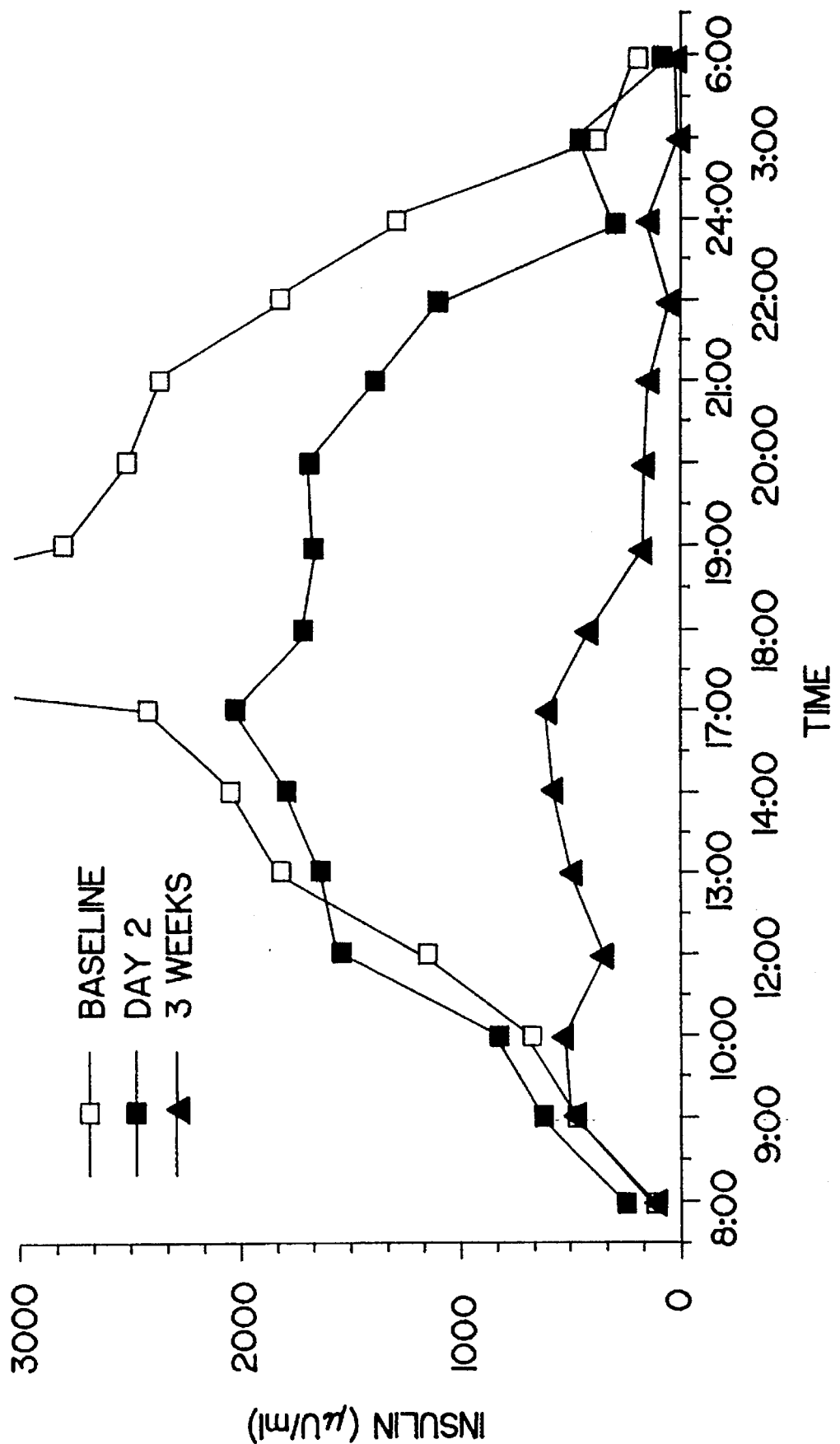
FIG. 2 depicts the effects of rhIGF-1 on serum insulin levels following 3 mixed meals and 2 snacks in a human subject with severe insulin resistance.

FIG. 2 depicts the effects of rhIGF-I on serum insulin levels following 3 mixed meals and 2 snacks in subject 1. Baseline data reflect serum insulin levels prior to therapy with IGF-I. Day 2 reflects data collected on the 2nd day of IGF-I administration (dose #2 and dose #3 administered at 8 AM and 5 PM respectively). 3 weeks represents data collected on the 22nd day of IGF-I administration with dosing of 100 μg/kg s.c. BID at 8 AM and 5 PM. The results show that rhIGF-I improved serum insulin levels within 36 hours of initiation of therapy and this effect was further improved after 3 weeks at which time IGF therapy was discontinued.

FIG. 3 shows blood glucose and serum insulin levels following an oral liquid mixed meal (Sustacal) at three time points in subject 1.

Figure 3B:
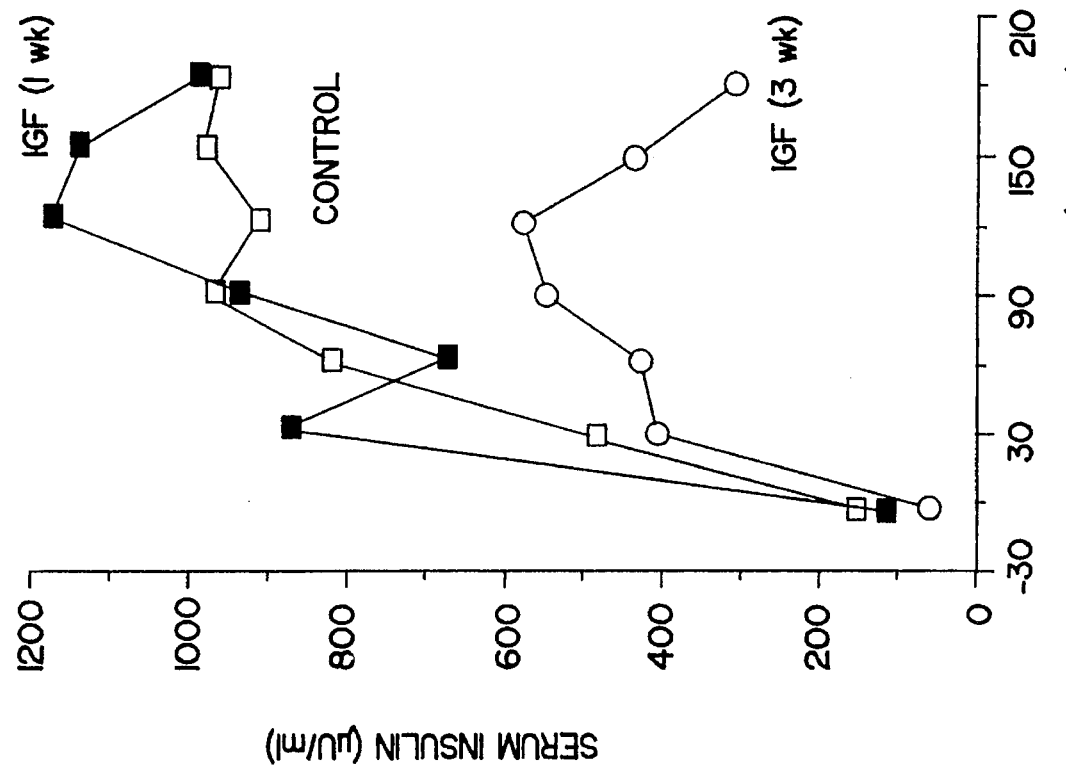
FIG. 3 (A and B) depicts blood glucose levels and serum insulin levels following an oral liquid mixed meal at three time points in a human subject with severe insulin resistance.
Figure 3A:
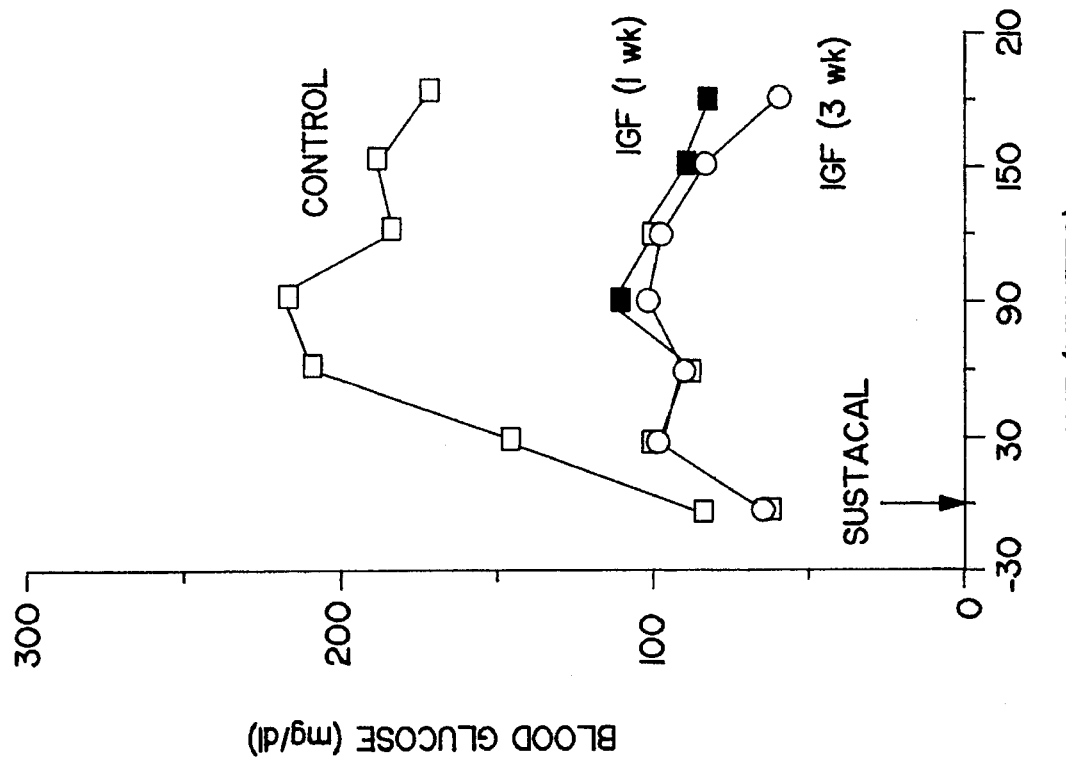

FIG. 3A depicts blood glucose concentrations measured every 30 minutes for 3 hours following oral ingestion of 250 ml of Sustacal in the Control period, following 1 week of rhIGF-I therapy, and following 3 weeks of rhIGF-I therapy. The data indicate the mean of duplicate determinations at each time point measured on a Yellow Springs glucose oxidase analyzer using venous whole blood collected in sodium flouride. Within one week of IGF-I treatment, glucose tolerance changed from overtly diabetic (by ADA criteria) to normal. Three week therapy maintained normal glycemic excursions.

FIG. 3B depicts serum insulin levels measured every 30 minutes for 3 hours following oral ingestion of 250 ml of Sustacal in the Control period, following 1 week of rhIGF-I therapy, and following 3 weeks of rhIGF-I therapy. The data indicate the mean of duplicate determinations performed on 1:5 dilutions of the subject's serum in a DPC radio immunoassay for insulin. There was no difference in the serum insulin profiles between the control period and after 1 week of IGF therapy. However, following three weeks of IGF-I, fasting serum insulin was lower and the excursion of insulin was much lower than the control period. This indicates that the effects of IGF-I on glucose homeostasis are complex. rhIGF-I appears to improve glucose tolerance before causing a dramatic reduction in serum insulin levels.

Figure 4:
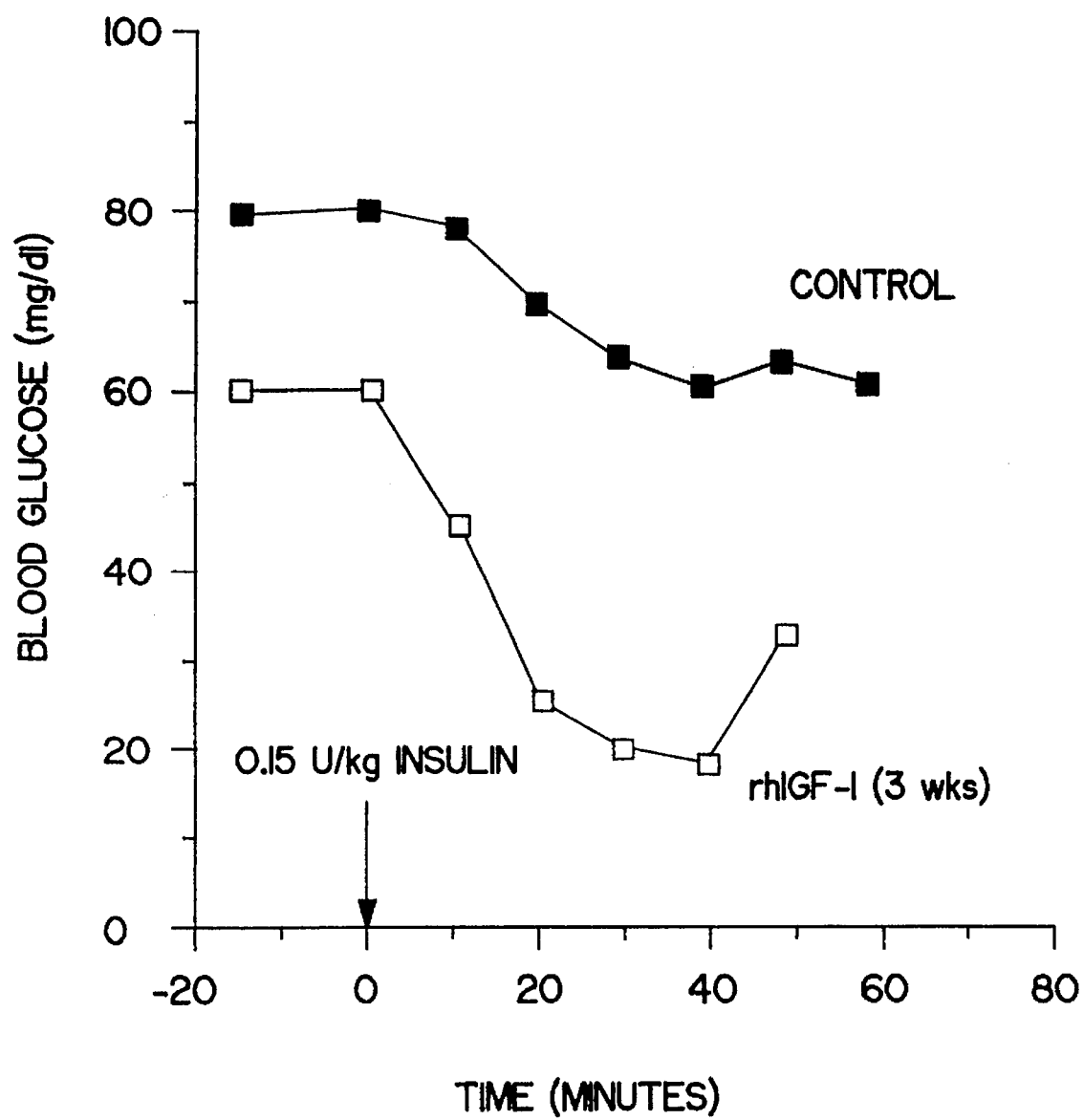
FIG. 4 depicts an insulin tolerance test in a human subject with severe insulin resistance.

FIG. 4 depicts an insulin tolerance test in subject 1. The blood glucose concentration was measured every 10 minutes for 60 minutes following the intravenous bolus of 0.15 U/kg of recombinant human insulin. In the control period (prior to rhIGF-I therapy), intravenous insulin is seen to have little effect on blood glucose concentration. This pattern is consistent with severe insulin resistance. Following 3 weeks of IGF-I therapy at 100 μg/kg s.c. BID, normal insulin sensitivity was restored.

Figure 5B:
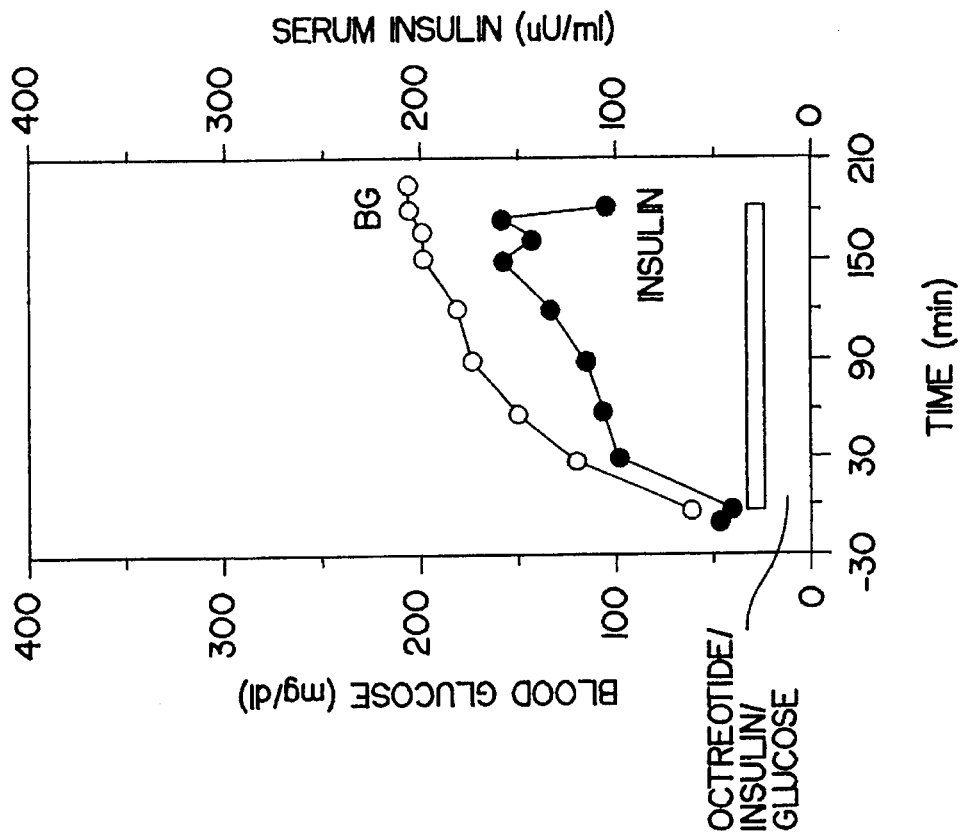
FIG. 5 (A and B) depicts steady state plasma glucose levels before and after rhIGF-1 therapy in a human subject.
Figure 5A:
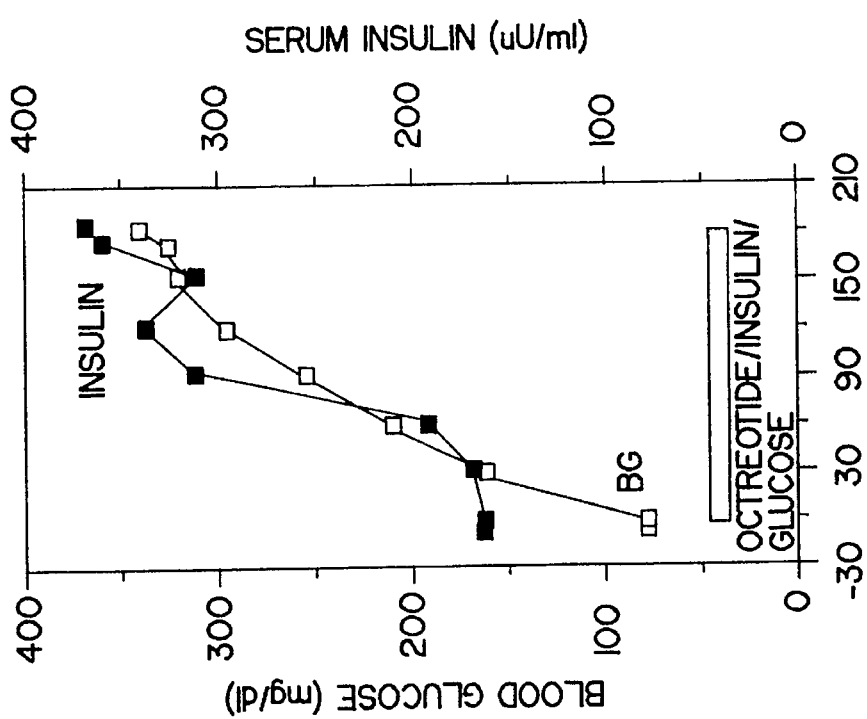

FIG. 5 depicts a steady state plasma glucose before and after rhIGF-I therapy. FIG. 5A shows the simultaneous infusion in the control period of octreotide (synthetic somatostatin, used to block endogenous insulin release), insulin, and glucose (both at fixed rates). As can be seen from the figure, blood glucose concentrations plateaued at 340 mg/dl with concomitant insulins of 350 μU/ml.

FIG. 5B shows the simultaneous infusion after rhIGF therapy of octreotide (synthetic somatostatin, used to block endogenous insulin release), insulin, and glucose (both at fixed rates). As can be seen from the figure, blood glucose levels plateaued at 200 mg/dl with plasma insulin levels at 150 uU/ml. Three weeks of therapy with rhIGF-I improved insulin sensitivity in a patient with severe insulin resistance. This increased insulin sensitivity was demonstrated both by a lower blood glucose level and by a lower serum insulin level required to achieve that blood glucose level. In addition, the data are compatible with the notion that the clearance of insulin is improved following rhIGF-I therapy.

EXAMPLE 2

A second human subject with severe insulin resistance and diabetes mellitus also enrolled in the above protocol to test the effectiveness of IGF-I. As with subject 1, all use of insulin or oral hypoglycemic agents was discontinued prior to the start of the protocol.

Subject 2 received the therapy for 28 consecutive days. The protocol of the first 22 days of therapy was virtually identical to the 22 day protocol of the first subject, and the findings as depicted in FIGS. 1–5 were similar.

The second subject continued the therapy for 28 days and was followed for at least 7 weeks beyond termination of administration of IGF-I.

Figure 6:
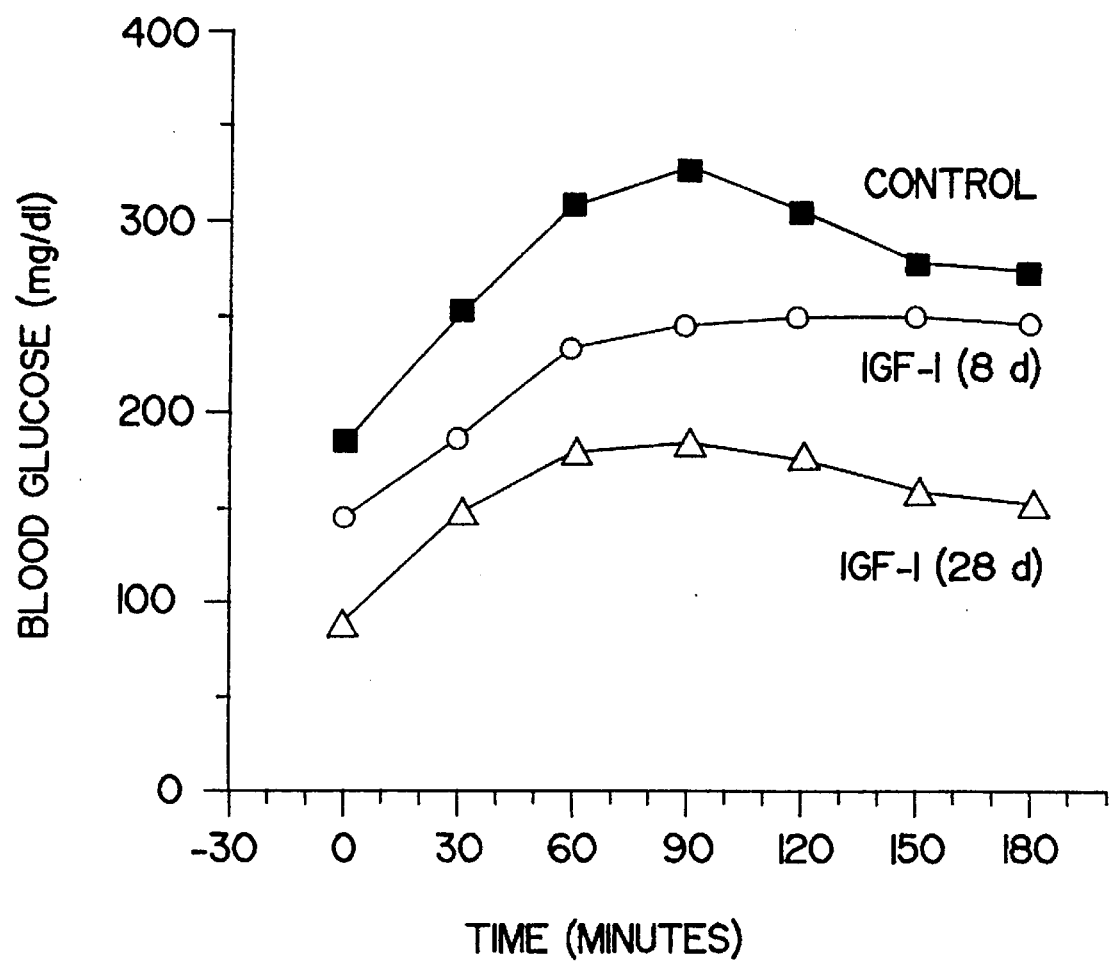
FIG. 6 depicts the blood glucose response to a liquid mixed meal consumed by a human subject with severe insulin resistance and diabetes mellitus.

FIG. 6 shows blood glucose response to a liquid mixed Sustacal meal in subject 2. The subject was treated with 100 μg/kg SC BID for 4 weeks and was administered 250 ml of Sustacal in the control period, following 8 days of rhIGF-I therapy and following 28 days of rhIGF-I therapy. The data points indicate the mean of duplicate determinations of blood glucose collected in sodium fluoride containing tubes on a Yellow Springs whole blood glucose analyzer. As can be seen on the figure, there was a progressive decline in blood glucose concentration over the three weeks of IGF-I therapy from overtly diabetic (Control) to near normal (28 days). This effect had never previously been observed over this time frame.

Figure 7:
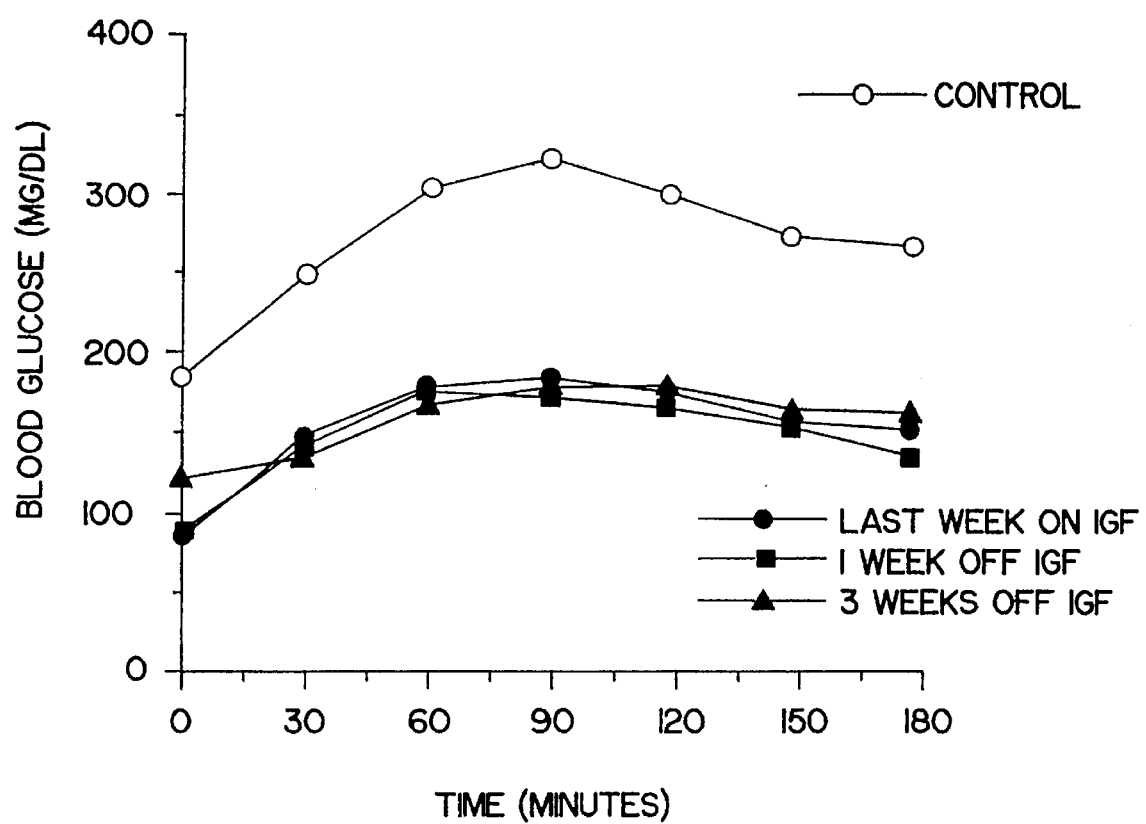
FIG. 7 depicts blood glucose levels in a human subject following a liquid mixed meal prior to rhIGF-I therapy, and blood glucose levels following a liquid mixed meal during the last week of IGF-I therapy (after 28 days of therapy).

FIG. 7 shows the result of a Sustacal challenge. The first shows the control blood glucoses (before rhIGF-I therapy) and the results during the last week of IGF-I (after 28 days of therapy) and results obtained 1 week and 3 weeks after the subject stopped taking rhIGF-I.

Figure 8:
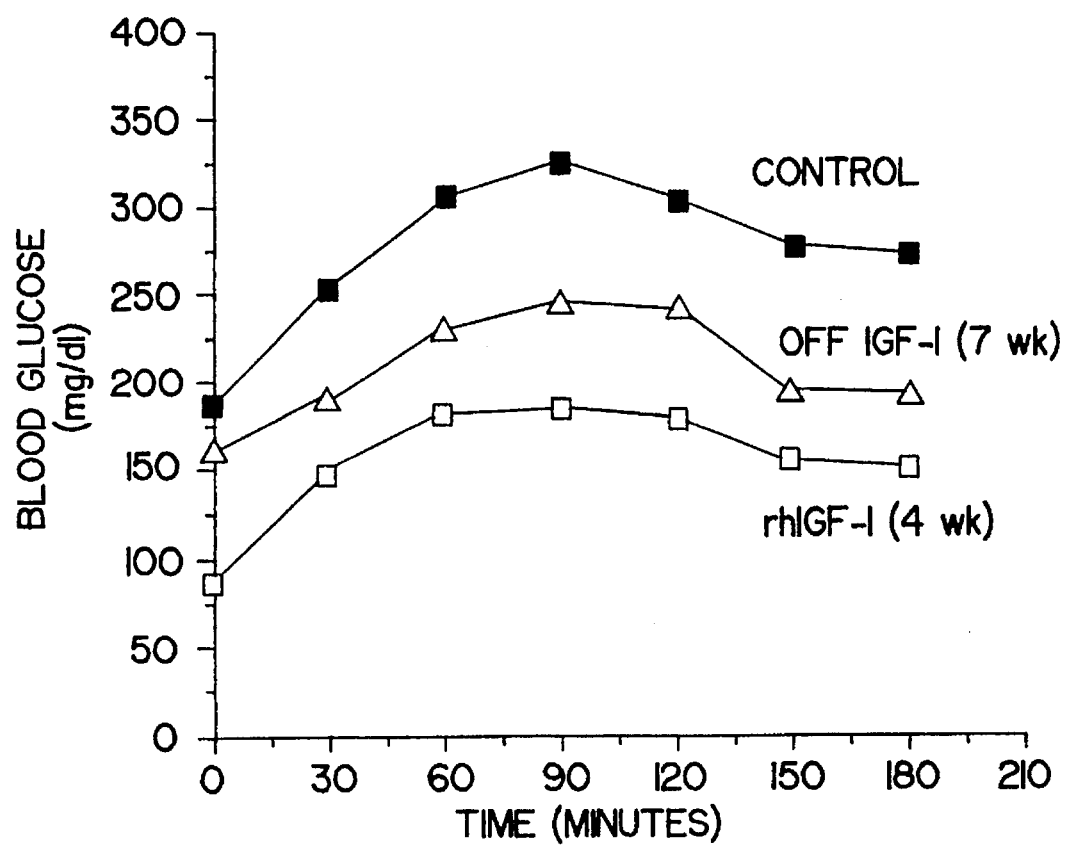
FIG. 8 depicts blood glucose levels in a human subject following a liquid mixed meal prior to rhIGF-1 therapy, and blood glucose levels following a liquid mixed meal obtained 4 weeks and 7 weeks after the discontinuation of IGF-I therapy.

FIG. 8 shows data from the control period, 4 weeks and 7 weeks respectively after the discontinuation of IGF-I. Seven weeks after the discontinuation of IGF-I, the blood glucoses are again elevated but are still lower than before the beginning of the treatment period.

What is claimed is:

1. A method of effecting chronic reversal of insulin resistance in humans with severe insulin resistance by administering rhIGF-I in a dose of 100 μg/kg body weight subcutaneously twice a day for about 21 consecutive days to about 28 consecutive days wherein said reversal persists at least about one week after concluding said administering.

2. The method of claim 1 wherein the rhIGF-I is administered for about 22 days.

* * * * *